US012582549B2

(12) United States Patent
Reyes

(10) Patent No.: US 12,582,549 B2
(45) Date of Patent: Mar. 24, 2026

(54) VITRECTOMY PROBE WITH MAGNETICALLY DRIVEN CUTTER

(71) Applicant: Alcon Inc., Fribourg (CH)

(72) Inventor: Nathaniel Reyes, Santa Ana, CA (US)

(73) Assignee: Alcon Inc., Fribourg (CH)

( * ) Notice: Subject to any disclaimer, the term of this patent is extended or adjusted under 35 U.S.C. 154(b) by 70 days.

(21) Appl. No.: 18/652,986

(22) Filed: May 2, 2024

(65) Prior Publication Data

US 2024/0390185 A1     Nov. 28, 2024

Related U.S. Application Data

(60) Provisional application No. 63/504,216, filed on May 25, 2023.

(51) Int. Cl.
A61F 9/007     (2006.01)
A61B 17/00     (2006.01)

(52) U.S. Cl.
CPC ..................... A61F 9/00736 (2013.01); A61B 2017/00398 (2013.01); A61B 2017/00876 (2013.01); A61B 2217/005 (2013.01)

(58) Field of Classification Search
CPC ......... A61B 2017/00876; A61B 2017/320032; A61B 2017/320028; A61B 2017/320024; A61B 17/32002; A61B 17/320016; A61F 9/00763; A61F 9/00736; A61F 9/00754; A61F 9/00745
See application file for complete search history.

(56) References Cited

U.S. PATENT DOCUMENTS

| | | | |
|---|---|---|---|
| 4,940,468 A | 7/1990 | Petillo | |
| 8,038,692 B2 | 10/2011 | Valencia | |
| 8,080,029 B2 | 12/2011 | Charles | |
| 8,888,802 B2 | 11/2014 | Underwood | |
| 9,060,841 B2 | 6/2015 | Mccawley | |
| 9,486,360 B2 | 11/2016 | Chon | |
| 10,251,782 B2 | 4/2019 | Farley | |
| 10,369,046 B2 | 8/2019 | Mcdonell | |
| 10,537,472 B2 | 1/2020 | Brennan | |
| 11,504,273 B2 | 11/2022 | Mcdonell | |
| 11,883,325 B2 | 1/2024 | Reyes | |
| 2008/0188881 A1 | 8/2008 | Chon | |
| 2011/0042597 A1 | 2/2011 | Huculak | |
| 2016/0120697 A1 | 5/2016 | Farley | |
| 2018/0104101 A1 | 4/2018 | Lopez | |
| 2018/0369016 A1* | 12/2018 | Underwood | ........ A61F 9/00763 |
| 2019/0099292 A1 | 4/2019 | Strayer | |
| 2022/0104969 A1 | 4/2022 | Reyes et al. | |
| 2023/0233747 A1 | 7/2023 | Sivadas | |

* cited by examiner

*Primary Examiner* — Majid Jamialahmadi

(57)     ABSTRACT

A vitrectomy probe includes a probe body and a needle portion projecting from the probe body. The needle portion includes a tube which extends at least partially in the needle portion and at least partially in the probe body. A cutter is positioned inside the tube in the needle portion. The cutter is at least partially composed of a permanently magnetic material. A field-creation unit is adapted to create an induced magnetic field, with the cutter being movable between a first position and a second position based in part on the induced magnetic field. The tube may be at least partially composed of a temporarily magnetic material. In one embodiment, the field-creation unit includes a driving magnet positioned in the probe body and adapted to selectively magnetize the tube.

11 Claims, 4 Drawing Sheets

VITRECTOMY PROBE WITH MAGNETICALLY DRIVEN CUTTER

INTRODUCTION

The disclosure relates generally to a vitrectomy probe. More specifically, the disclosure relates to a vitrectomy probe having a cutter that is driven with the aid of a magnetic field. Humans have five basic senses: sight, hearing, smell, taste, and touch. Sight gives us the ability to visualize the world around us and connects us to our surroundings. Many people worldwide have issues with their quality of vision. Treatment options for some of the issues affecting vision quality may include vitreoretinal surgery. During vitreoretinal surgery, a vitrectomy probe is used to remove ocular components such as membranes, tissues and vitreous humor. The vitrectomy probe has a port for drawing in the ocular components, which are then aspirated away. Many vitrectomy probes include a cutter that is mechanically driven by an engine at the rear of the probe, requiring the cutter to extend towards the rear of the probe.

SUMMARY

Disclosed herein is a vitrectomy probe having a probe body and a needle portion projecting from the probe body. The needle portion includes a tube which extends at least partially in the needle portion and at least partially in the probe body. A cutter is positioned inside the tube in the needle portion. The cutter is at least partially composed of a permanently magnetic material. A field-creation unit is adapted to create an induced magnetic field, with the cutter being movable between a first position and a second position based in part on the induced magnetic field.

The tube may be at least partially composed of a temporarily magnetic material. In one embodiment, the field-creation unit includes a driving magnet positioned in the probe body. The field-creation unit in such an embodiment is adapted to selectively magnetize the tube such that movement in the cutter is induced when the tube is magnetized.

Another aspect of the disclosure includes an actuator adapted to selectively move the driving magnet, with the driving magnet being a permanent magnet, and the tube being magnetized when the driving magnet is moved. A controller may be adapted to change the orientation of the driving magnet relative to the tube in order to induce the movement of the cutter in a reverse direction.

In some embodiments, the tube is at least partially composed of a temporarily magnetic material. Here, the field-creation unit includes an electromagnet positioned in the probe body and coiled around the tube. A flow of electric current in the electromagnet selectively magnetizes the tube, with the magnetized tube inducing movement in the cutter.

Another aspect of the disclosure includes a spring operatively connected to the cutter and adapted to bias the cutter in the first position. The tube may include a first port adapted to receive aspirated tissue and the cutter includes a second port at least partially coextensive with the first port. In some embodiments, a respective length of the needle portion is about three to six times greater than the respective length of the cutter. The respective length of the needle portion may be at least five times greater than the respective length of the cutter.

In some embodiments, the field-creation unit includes a wire positioned around the tube in sufficient proximity to the cutter such that flow of an electric current through the wire induces movement of the cutter. A controller adapted to adjust a polarity of the electric current to alter the direction of the movement of the cutter, the controller having a processor and a non-transitory, tangible memory on which instructions are recorded.

Also disclosed herein is a vitrectomy probe having a probe body and a needle portion projecting from the probe body. A tube extends at least partially in the needle portion and at least partially in the probe body, the tube being at least partially composed of a temporarily magnetic material. A cutter is positioned inside the tube in the needle portion, the cutter being movable relative to the tube, the cutter being at least partially composed of a permanently magnetic material. The vitrectomy probe includes a field-creation unit having an electromagnet positioned in the probe body and coiled around the tube. A flow of electric current in the electromagnet selectively magnetizes the tube, with the magnetized tube inducing movement in the cutter.

The above features and advantages and other features and advantages of the present disclosure are readily apparent from the following detailed description of several embodiments for carrying out the disclosure when taken in connection with the accompanying drawings.

Figure 1:
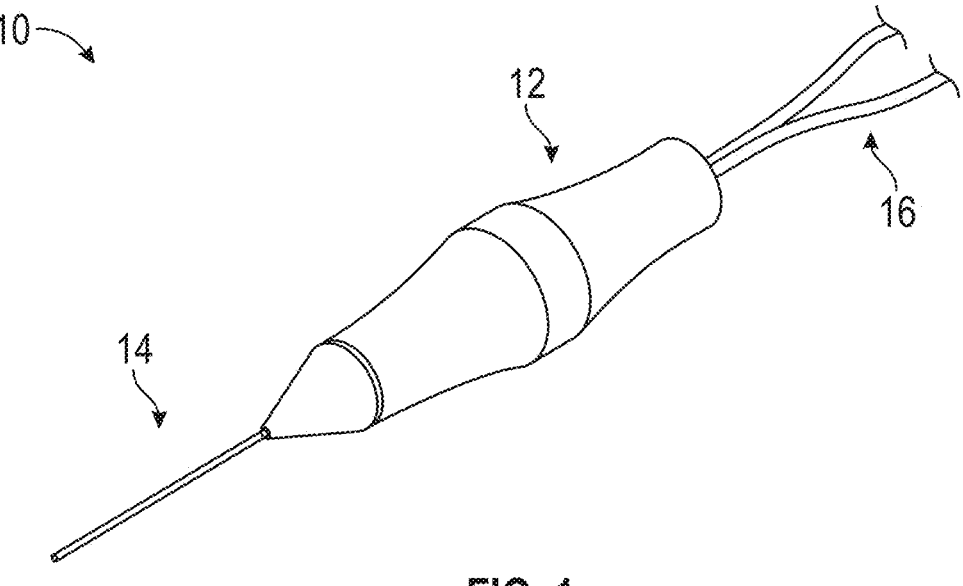
FIG. 1 is a schematic illustration of a vitrectomy probe having a needle portion projecting from a probe body.

Representative embodiments of this disclosure are shown by way of non-limiting example in the drawings and are described in additional detail below. It should be understood, however, that the novel aspects of this disclosure are not limited to the particular forms illustrated in the above-enumerated drawings. Rather, the disclosure is to cover modifications, equivalents, combinations, sub-combinations, permutations, groupings, and alternatives falling within the scope of this disclosure as encompassed, for instance, by the appended claims.

DETAILED DESCRIPTION

Figure 2A:
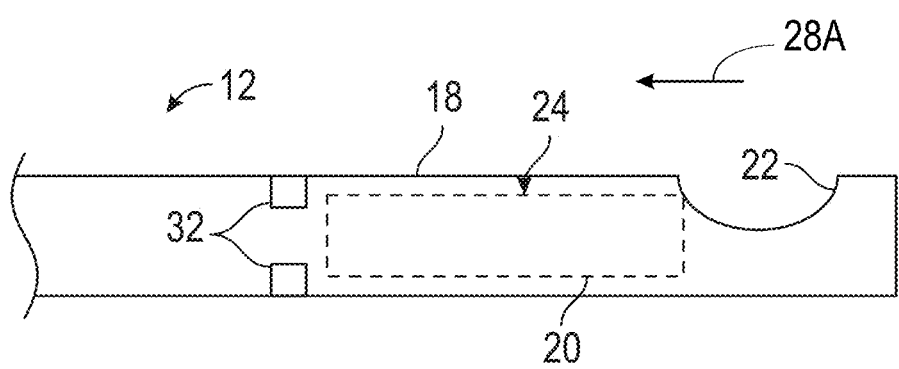
FIG. 2A is a schematic fragmentary diagram of the needle portion of FIG. 1 having a cutter in a first position.
Figure 2B:
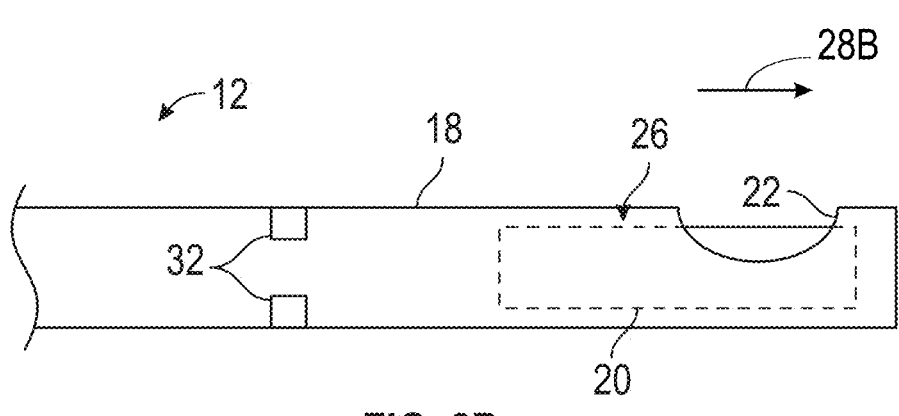
FIG. 2B is a schematic fragmentary diagram of the needle portion of FIG. 2A, with the cutter in a second position.

Referring to the drawings, wherein like reference numbers refer to like components, FIG. 1 schematically illustrates a vitrectomy probe 10 having a probe body 12 with a portion projecting or extending from it, referred to herein as needle portion 14. The probe body 12 is graspable by an operator, such as a surgeon, during ocular surgery. During ocular surgery, the needle portion 14 may be inserted into the posterior segment of an eye. FIGS. 2A-2B show a schematic fragmentary diagram of the needle portion 14. The needle portion 14 includes a tube 18 with a cutter 20 positioned inside the tube 18. The cutter 20 may be actuated to sever or "cut" various types of ocular components, such as vitreous humor, membranes covering the retina, the lens, and other tissue. The tube 18 includes a first port 22 (see FIGS. 2A-2B) for drawing in the ocular components. The ocular components may be aspirated away through the tube 18 and directed towards aspiration channels 16 (see FIG. 1).

The cutter 20 is movable between a first position 24 (shown in FIG. 2A) and a second position 26 (shown in FIG. 2B). The cutter 20 is movable along a first direction 28A (see FIG. 2A) and/or a second direction 28B (see FIG. 2B) based in part on an induced magnetic field which is created by a field-creation unit 130, 230, 330, described below with respect to FIGS. 3, 4, and 5, respectively. The actuation of the cutter 20 may be rotationally continuous, rotationally reciprocating, translationally reciprocating and otherwise. Referring to FIGS. 2A-2B, the tube 18 may include a structural member, referred to herein as stop 32, to restrict the reverse movement of the cutter 20.

The cutter 20 is composed at least partially of a permanently magnetic material. The tube 18 may be at least partially composed of a temporarily magnetic material. Magnets may be broadly classified into permanent magnets and temporary magnets (electromagnets). A permanent magnet retains its magnetic properties for a long period of time. Examples of permanently magnetic materials include iron, nickel, cobalt, ceramic, and some rare earth alloys such as neodymium iron boron. Temporary magnets act like permanent magnets when they are within a strong magnetic field but lose their magnetism when the magnetic field disappears. Examples of temporarily magnetic material include soft metals such as soft iron.

Many probes include a cutter that is mechanically driven by an engine at the rear of the probe, requiring the cutter to extend towards the rear of the probe. A longer cutter has additional mass, resulting in greater inertia and more energy needed to drive. Moreover, the cutter may be attached to an extension tube and diaphragm, which add further mass.

As described below, having a cutter 20 that is magnetically driven allows the cutter to be relatively short. Since the cutter 20 is smaller, less energy is needed to actuate it and thus less energy is transmitted to the probe body 12 when the cutter 20 switches direction, allowing for faster actuation speeds and less vibration. Having a cutter 20 be smaller in length increases the amount of cross-sectional area available for aspiration, since the diameter constriction caused by the cutter 20 would be limited to the length of the cutter. This widens the aspirational flow path from the inner diameter of the cutter to the inner diameter of the tube for the majority of the flow length. This potential increase is governed by the Hagen-Poiseuille equation, where $$\Delta p = \left[ \frac{8\mu L Q}{\pi R^4} \right].$$

Here $\Delta p$ is the drop in pressure, $\mu$ is the dynamic viscosity, L is the length of the tube, Q is the volumetric flow rate, and R is the internal radius of the tube. Assuming that the drop in pressure, dynamic viscosity, and the tube length are similar, the following relationship will hold:

$$\frac{Qnew}{Qold} = \left[ \frac{Rnew}{Rold} \right]^4.$$

For example, this may result in the flow rate tripling, relative to other probes.

Figure 3:
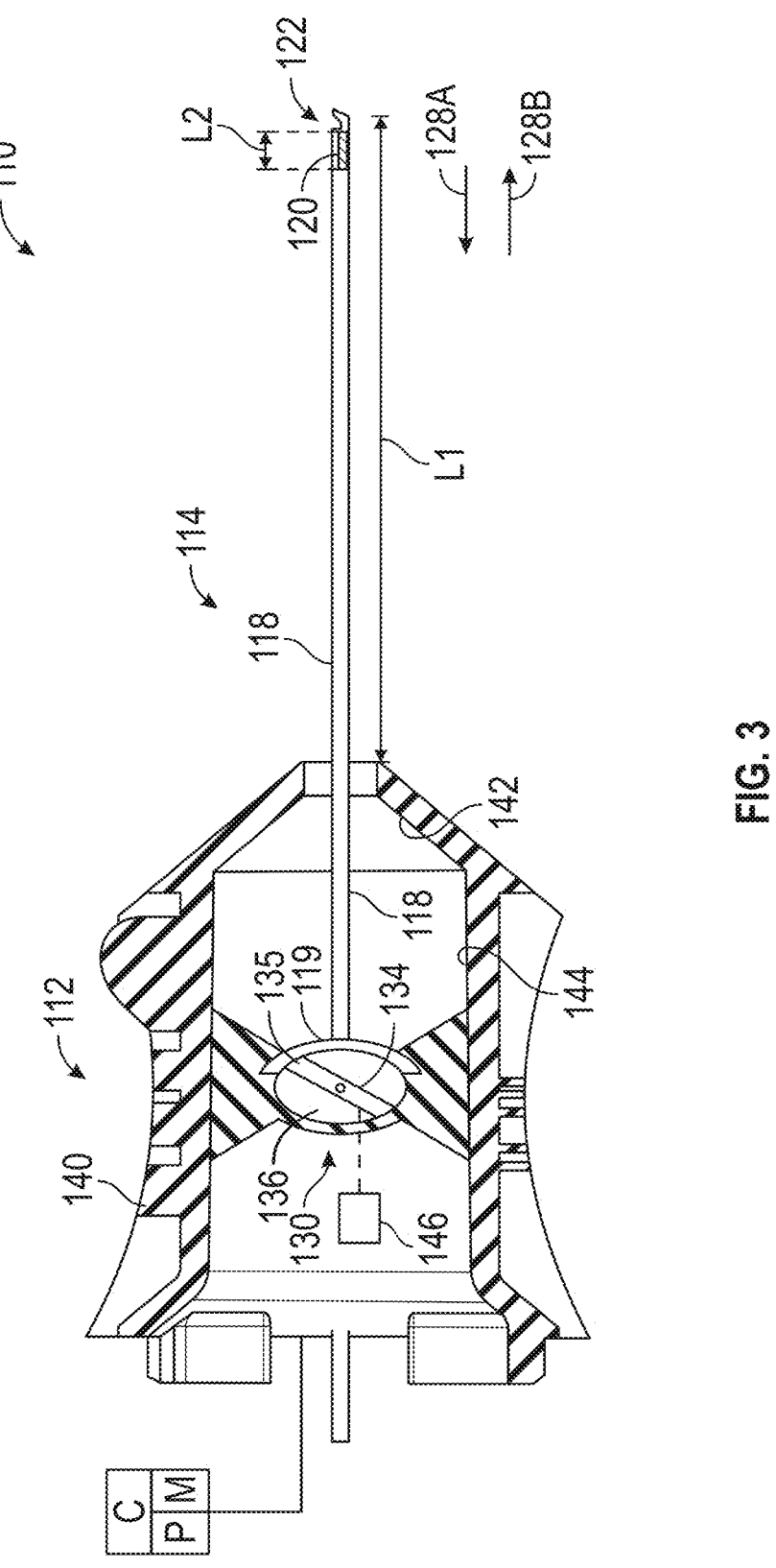
FIG. 3 is a schematic fragmentary sectional view of another example vitrectomy probe.

The cutter 20 may be magnetically driven in several different ways. FIGS. 3-6 show various examples of vitrectomy probes where the cutter 20 is driven by an induced magnetic field. Referring now to FIG. 3, the example vitrectomy probe 110 has a probe body 112 with a portion projecting or extending from it, referred to herein as needle portion 114. The probe body 112 may be graspable by an operator and the needle portion 114 may be inserted into an eye. The needle portion 114 includes a tube 118 with a cutter 120 positioned inside the tube 118. The tube 118 extends at least partially in the needle portion and at least partially in the probe body 112. The tube 118 includes a first port 122 for aspirating ocular components. It is understood that the probe body 112 may take many different forms and include multiple and/or alternate components and facilities.

In the embodiment shown in FIG. 3, the tube 118 is adapted to transmit magnetic force to induce movement in the cutter 120. The tube 118 is at least partially composed of a temporarily magnetic material. The vitrectomy probe 110 includes a field-creation unit 130 having a driving magnet 134. The probe body 112 is defined by a housing 140. The driving magnet 134 is enclosed within a cavity 136 in the housing 140. Referring to FIG. 3, the housing 140 includes an anterior chamber 142 and a posterior chamber 144. Here, the posterior chamber 144 has a relatively constant diameter while the anterior chamber 142 has an inclined slope with a variable diameter. The housing 140 may include other support mechanisms, such as rods, attachments, and fasteners.

The driving magnet 134 is a permanent magnet such that the tube 118 is magnetized upon motion of the driving magnet 134. The driving magnet 134 is rotated mechanically within the cavity 136 by an actuation mechanism 146 (e.g., pneumatics, chain drive, etc.). In the embodiment shown in FIG. 3, the driving magnet 134 may be rotated clockwise and counterclockwise. The tube 118 may be formed with a tube base 119 that is substantially hemispherical in shape. During part of the rotation, the driving magnet 134 magnetizes the tube 118 with a first pole (e.g., north pole) in contact with the tube base 119, causing the cutter 120 to move in one direction (e.g., first direction 128A). When the driving magnet 134 is rotated 180 degrees from its original position, the magnetic polarity flips since the opposite pole (e.g., south pole) of the driving magnet 134 is now in contact (at contact point 135) with the tube base 119. This causes the direction of motion of the cutter 120 to reverse (e.g., second direction 128B).

The actuator 146 may employ a mechanism available to those skilled in the art, such as an active solenoid. The actuator 146 may incorporate a piezoelectric actuator that converts an electrical signal into a precisely controlled physical displacement. The actuator 146 may include a shape memory alloy which undergoes reversible deformation through application of heat. The actuator 146 may be controlled through a controller C. Referring to FIG. 3, the controller C includes at least one processor P and at least one memory M (or non-transitory, tangible computer readable storage medium) on which instructions may be recorded for controlling the motion of the driving magnet 134 by the actuator 146, thereby controlling the movement of the cutter 120. The memory M can store controller-executable instruction sets, and the processor P can execute the controller-executable instruction sets stored in the memory M.

In some embodiments, the driving magnet 134 may be adapted to spin continuously in one direction (e.g., just clockwise), rather than oscillating, which enables a simpler actuation mechanism while retaining the same effect of switching the polarity of the tube 118. For example, the actuation mechanism 146 may incorporate one-way fluid flow through a turbine, or a one-way motion of a drive chain around a gear, to produce continuous one-way rotation. The speed of rotation of the driving magnet 134 determines the rate at which the polarity switches. During an initial position (at 0 degrees) of the driving magnet 134 the tube 118 is in contact with a first pole (e.g., the north pole) of the driving magnet 134. The tube 118 is in contact with the opposite pole (e.g., south pole) when the driving magnet 134 reaches a half rotation (180 degrees). When the driving magnet 134 completes a full rotation (360 degrees), the tube 118 would be in contact with the first pole again, and so on.

As shown in FIG. 3, the respective length L1 of the needle portion 114 is greater than the respective length L2 of the cutter 120. The respective length L1 and the respective length L2 are measured along the direction of motion of the cutter 120, i.e., along direction 128A or 128B. In one example, the respective length L1 of the needle portion 114 is about 3 to 6 times greater than the respective length L2 of the cutter 120. In another example, the respective length L1 of the needle portion 114 is at least 5 times greater than the respective length L2 of the cutter 120.

Figure 4:
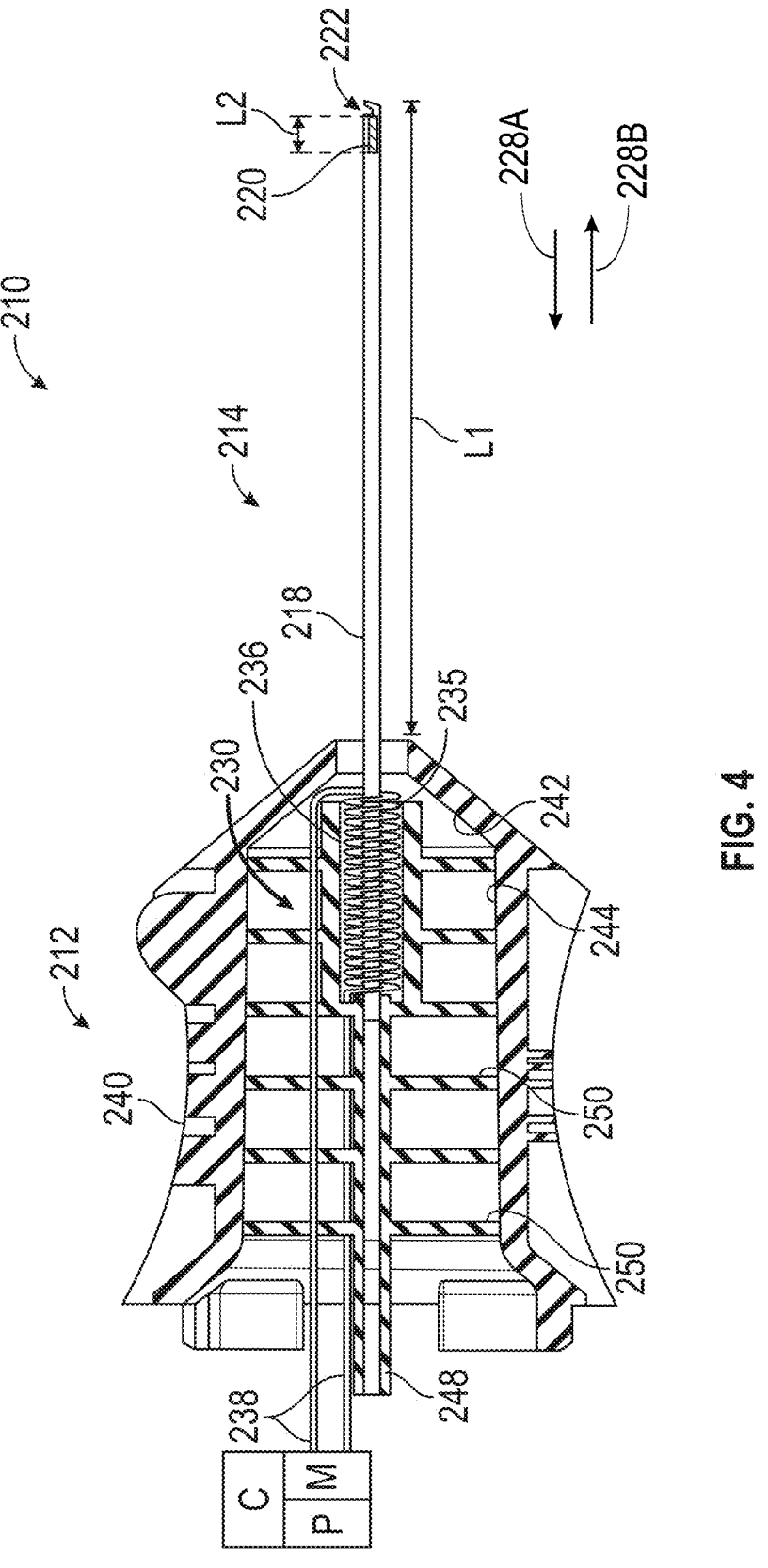
FIG. 4 is a schematic fragmentary sectional view of yet another example vitrectomy probe.

Referring now to FIG. 4, a schematic fragmentary view of another example vitrectomy probe 210 is shown. The vitrectomy probe 210 has a probe body 212 with a portion projecting or extending from it, referred to herein as needle portion 214. The probe body 212 may be graspable by an operator and the needle portion 214 may be inserted into an eye. The needle portion 214 includes a tube 218 with a cutter 220 positioned inside the tube 218. The tube 218 includes a first port 222 for removing ocular components. The tube 218 extends at least partially in the needle portion and at least partially in the probe body 212.

In the embodiment shown in FIG. 4, the tube 218 is at least partially composed of a temporarily magnetic material. The vitrectomy probe 210 includes a field-creation unit 230 having an electromagnet 235. The electromagnet 235 is placed near the tube 218 (e.g., coiled around the tube 218) such that a flow of electric current in the electromagnet 235 selectively magnetizes the tube 218. The tube 218 is least partially composed of a temporarily magnetic material. This would in turn oscillate the cutter 220, which is at least partially composed of a permanently magnetic material.

In other words, a flow of electric current through the electromagnet 235 is used to induce magnetism (that oscillates in direction) in the tube 218. Movement of the cutter 220 is caused by the induced magnetic field created by the magnetized tube 218. As noted above, a permanently magnetic material retains its magnetic properties for a long period of time. Examples of permanently magnetic materials include iron, nickel, cobalt, ceramic, and some rare earth alloys such as neodymium iron boron. Temporary magnets act like permanent magnets when they are within a strong magnetic field but lose their magnetism when the magnetic field disappears.

The flow of electric current in the electromagnet 235 may be controlled through a controller C. The electromagnet 235 may be connected to the controller C through connectors 238. The controller C is adapted to reverse the polarity of the electric current to move the cutter 220 in a reverse direction (e.g., from first direction 228A to second direction 228B and vice versa, sec FIG. 4).

Referring to FIG. 4, the controller C includes at least one processor P and at least one memory M (or non-transitory, tangible computer readable storage medium) on which instructions may be recorded for controlling the actuation of the cutter 220 via the flow of electric current in the electromagnet 235. The memory M can store controller-executable instruction sets, and the processor P can execute the controller-executable instruction sets stored in the memory M.

The electromagnet 235 is electrically stimulated to alternate between polarities and thereby produce alternating polarities in the tube 218; this in turn produces reciprocating motion on the magnetized cutter 220. Alternatively, the electromagnet 235 may be used to drive the cutter 220 in only one direction, while the return motion may be achieved via a mechanical apparatus (e.g., a spring 462 shown in FIG. 6).

Referring to FIG. 4, the probe body 212 is defined by a housing 240. The electromagnet 235 is positioned within a cavity 236 in the housing 240. Referring to FIG. 4, the housing 240 includes an anterior chamber 242 and a posterior chamber 244. Here, the posterior chamber 244 has a relatively constant diameter while the anterior chamber 242 has an inclined slope with a variable diameter. The housing 240 may include a support rod 248 and support pillars 250 to support the tube 218 along the length of the probe body 212. It is understood that the probe body 212 may take many different forms and include multiple and/or alternate components and facilities.

As shown in FIG. 4, the respective length L1 of the needle portion 214 is greater than the respective length L2 of the cutter 220. In one example, the respective length L1 of the needle portion 214 is about 3 to 6 times greater than the respective length L2 of the cutter 220. In another example, the respective length L1 of the needle portion 214 is at least 5 times greater than the respective length L2 of the cutter 220.

Figure 5:
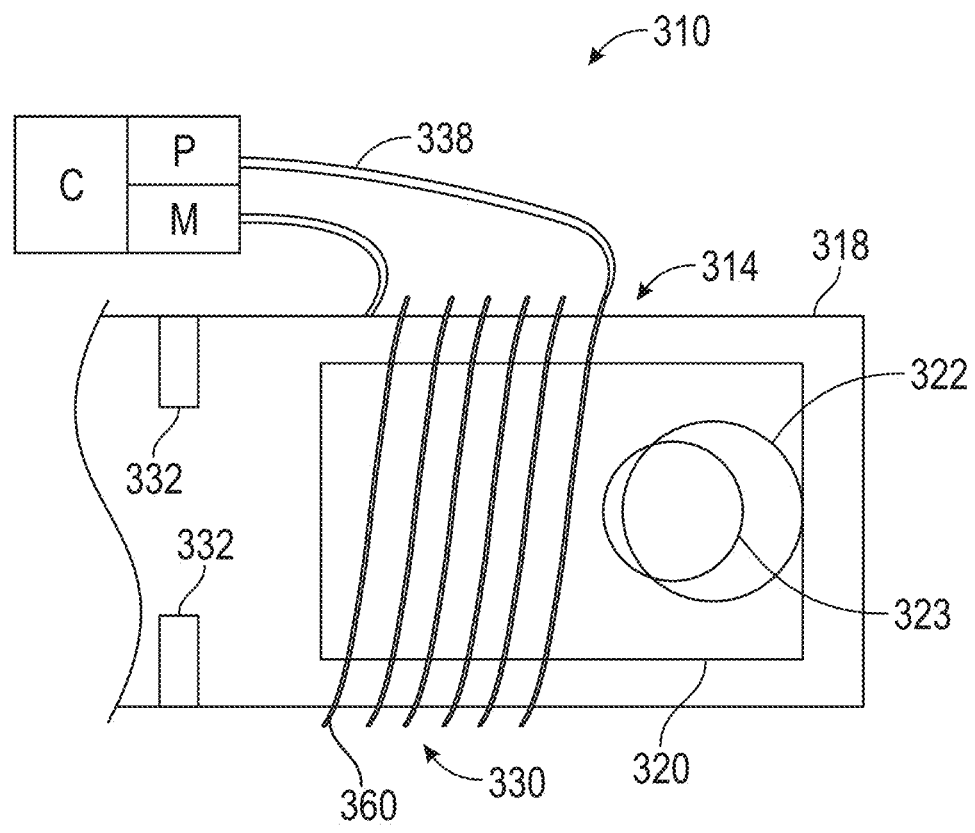
FIG. 5 is a schematic fragmentary diagram of yet another example vitrectomy probe.

FIG. 5 is a schematic fragmentary view of another example vitrectomy probe 310 having a needle portion 314. The needle portion 314 includes a tube 318 with a cutter 320 positioned within. The tube 318 includes a first port 322 for removing ocular components. Referring to FIG. 5, the cutter 320 has a second port 323 for retrieving and aspirating tissue. The second port 323 is at least partially coextensive with the first port 322. In the embodiment shown, the cutter 320 is free-standing or free-floating, i.e., not directly attached to any supporting structure. Movement of the cutter 320 may be restricted by stops 332 positioned within the tube 318.

The vitrectomy probe 310 of FIG. 5 includes a field-creation unit 330 with at least one electrical wire 360 positioned around the tube 318 in sufficient proximity to the cutter 320 such that flow of an electric current through the electrical wire 360 creates an induced magnetic field. The cutter 320 is at least partially composed of a permanently magnetic material and is compelled to move by the induced magnetic field. Stated differently, the electrical wire 360 is placed in a manner (e.g., wrapped around the circumference of the tube 318 at the location of the cutter 320) that would cause the cutter 320 to be moved by electromagnetic force when electric current flows through the electrical wire 360.

The flow of electric current in the electrical wire 360 may be controlled to produce alternating translational motion in the magnetized cutter, through a controller C. The controller C is adapted to reverse the polarity of the electric current to move the cutter 320 in a reverse direction (e.g., from first direction 28A to second direction 28B and vice-versa, see FIGS. 2A-2B). The electrical wire 360 may be connected to the controller C through connectors 338.

Referring to FIG. 5, the controller C includes at least one processor P and at least one memory M (or non-transitory, tangible computer readable storage medium) on which instructions may be recorded for controlling the actuation of the cutter 320 via the flow of electric current in the electrical wire 360. The memory M can store controller-executable instruction sets, and the processor P can execute the controller-executable instruction sets stored in the memory M.

Figure 6:
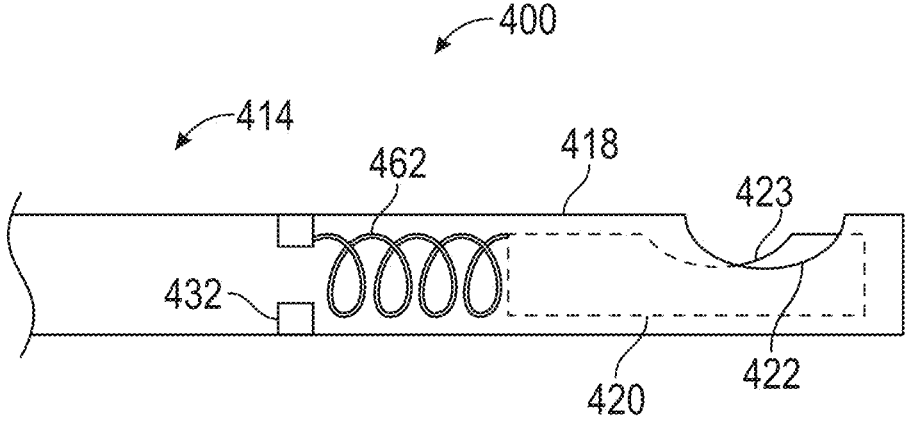
FIG. 6 is a schematic fragmentary diagram of an example biasing mechanism employable by the vitrectomy probes of FIGS. 3-5.

Each of the field-creation units 130, 230, 330 (described above with respect to FIGS. 3, 4 and 5) may be used to drive the cutter in only one direction, with the return motion being achieved via a mechanical biasing apparatus. An example biasing mechanism 400 is shown in FIG. 6. A cutter 420 is located inside of a tube 418 in a needle portion 414. The biasing mechanism 400 includes a spring 462 that is operatively connected to the cutter 420 and adapted to bias the cutter 420 in a resting position. In other words, the field-creation units 130, 230, 330 (of FIGS. 3, 4 and 5, respectively) may be used to drive the cutter 420 away from its resting position, with the spring 462 causing it to return to its resting position (e.g., first position 24 in FIG. 2A). The spring 462 may be connected to a support member 432 in the tube 418. Referring to FIG. 6, the cutter 420 may include a second port 423 that is at least partially coextensive with a first port 422 in the tube 418, thereby providing an additional or wider flow path for the removed ocular components.

In summary, various examples of vitrectomy probes are shown where the cutter 20, 120, 220, 320, 420 is driven by an induced magnetic field. The cutter 20, 120, 220, 320, 420 is at least partially composed of a permanently magnetic material. Having a cutter 20, 120, 220, 320, 420 that is magnetically driven allows it to be smaller in length along the direction of motion, reducing the amount of energy needed for actuation of the cutter and increasing the amount of cross-sectional area available for aspiration of ocular components. In some embodiments, the cutter (e.g., cutter 320 in FIG. 5) is free-standing or free-floating, i.e., not directly attached to any supporting structure.

The controller C of FIGS. 3-5 includes a computer-readable medium (also referred to as a processor-readable medium), including a non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random-access memory (DRAM), which may constitute a main memory. Such instructions may be transmitted by one or more transmission media, including coaxial cables, copper wire and fiber optics, including the wires that comprise a system bus coupled to a processor of a computer. Some forms of computer-readable media include, for example, a floppy disk, a flexible disk, hard disk, magnetic tape, other magnetic medium, a CD-ROM (Compact Disc Read Only Memory), DVD (Digital Versatile Disc), other optical medium, punch cards, paper tape, other physical medium with patterns of holes, a RAM (Random Access Memory), a PROM (Programmable Read-Only Memory), an EPROM (Erasable Programmable Read-Only Memory), a FLASH-EEPROM (Electrically erasable programmable read-only memory), other memory chip or cartridge, or other medium from which a computer can read.

Look-up tables, databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc.

Each such data store may be included within a computing device employing a computer operating system such as one of those mentioned above and may be accessed via a network in one or more of a variety of manners. A file system may be accessible from a computer operating system and may include files stored in various formats. An RDBMS may employ the Structured Query Language (SQL) in addition to a language for creating, storing, editing, and executing stored procedures, such as the PL/SQL (Procedural Language Extensions to the Structured Query Language) language mentioned above.

The detailed description and the drawings or FIGS. are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings, or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. A vitrectomy probe comprising:
a probe body and a needle portion projecting from the probe body;
the needle portion including a tube extending at least partially in the probe body, the tube is at least partially composed of a temporarily magnetic material;
a cutter positioned inside the tube, the cutter being movable relative to the tube, the cutter being at least partially composed of a permanently magnetic material; and
a field-creation unit adapted to create an induced magnetic field, the cutter being movable between a first position and a second position based in part on the induced magnetic field, the field-creation unit includes an electromagnet positioned in the probe body and coiled around the tube; and
wherein a flow of electric current in the electromagnet selectively magnetizes the tube, the magnetized tube inducing movement in the cutter.

2. The vitrectomy probe of claim 1, further comprising:
a spring operatively connected to the cutter and adapted to bias the cutter in the first position.

3. The vitrectomy probe of claim 1, wherein the tube includes a first port adapted to receive aspirated tissue and the cutter includes a second port at least partially coextensive with the first port.

4. The vitrectomy probe of claim 1, wherein a respective length of the needle portion is about three to six times greater than the respective length of the cutter.

5. The vitrectomy probe of claim 1, wherein a respective length of the needle portion is at least five times greater than the respective length of the cutter.

6. The vitrectomy probe of claim 1, wherein:
the field-creation unit includes a wire positioned around the tube in sufficient proximity to the cutter such that flow of an electric current through the wire induces movement of the cutter.

7. The vitrectomy probe of claim 6, further comprising:

a controller adapted to adjust a polarity of the electric current to alter a direction of the movement of the cutter, the controller having a processor and a non-transitory, tangible memory on which instructions are recorded.

8. A vitrectomy probe comprising:

a probe body and a needle portion projecting from the probe body;

the needle portion including a tube extending at least partially in the probe body, the tube being at least partially composed of a temporarily magnetic material;

a cutter positioned inside the tube, the cutter being movable relative to the tube, the cutter being at least partially composed of a permanently magnetic material; and a field-creation unit including an electromagnet positioned in the probe body and coiled around the tube; and wherein a flow of electric current in the electromagnet selectively magnetizes the tube, the magnetized tube inducing movement in the cutter.

9. The vitrectomy probe of claim 8, wherein a respective length of the needle portion is about three to six times greater than the respective length of the cutter.

10. The vitrectomy probe of claim 8, further comprising:

a controller adapted to adjust a polarity of the electric current to alter a direction of the movement of the cutter, the controller having a processor and a non-transitory, tangible memory on which instructions are recorded.

11. The vitrectomy probe of claim 8, wherein the tube includes a first port adapted to receive aspirated tissue and the cutter includes a second port at least partially coextensive with the first port.

*    *    *    *    *